United States Patent
Lowry et al.

(10) Patent No.: US 7,867,263 B2
(45) Date of Patent: Jan. 11, 2011

(54) IMPLANTABLE BONE PLATE SYSTEM AND RELATED METHOD FOR SPINAL REPAIR

(75) Inventors: David Lowry, Holland, MI (US); Desmond O'Farrell, East Grand Rapids, MI (US); Scott Tuinstra, Holland, MI (US); Roger Veldman, Hudsonville, MI (US)

(73) Assignee: TransCorp, Inc., Byron Center, MI (US)

( * ) Notice: Subject to any disclaimer, the term of this patent is extended or adjusted under 35 U.S.C. 154(b) by 250 days.

(21) Appl. No.: 11/855,124

(22) Filed: Sep. 13, 2007

(65) Prior Publication Data

US 2009/0043340 A1 Feb. 12, 2009

Related U.S. Application Data

(60) Provisional application No. 60/954,511, filed on Aug. 7, 2007.

(51) Int. Cl.
*A61B 17/88* (2006.01)
*A61B 17/80* (2006.01)
*A61B 17/66* (2006.01)

(52) U.S. Cl. ............... 606/281; 606/279; 606/280; 623/17.11; 623/17.16

(58) Field of Classification Search ......... 606/280–282, 606/86 R, 90, 99, 246, 279; 623/17.11
See application file for complete search history.

(56) References Cited

U.S. PATENT DOCUMENTS

| | | | |
|---|---|---|---|
| 3,741,205 A * | 6/1973 | Markolf et al. ............... 606/291 |
| 5,059,194 A | 10/1991 | Michelson | |
| 5,246,458 A | 9/1993 | Graham | |
| 5,306,275 A | 4/1994 | Bryan | |
| 5,423,826 A | 6/1995 | Coates et al. | |

(Continued)

FOREIGN PATENT DOCUMENTS

DE 4434384 A1 3/1996

(Continued)

OTHER PUBLICATIONS

Lowry et al.; U.S. Appl. No. 12/188,131 entitled "Device and method for variably adjusting intervertebral distraction and lordosis," filed Aug. 7, 2008.

(Continued)

*Primary Examiner*—Thomas C Barrett
*Assistant Examiner*—Michael T Schaper
(74) *Attorney, Agent, or Firm*—Shay Glenn LLP

(57) ABSTRACT

A system for performing surgical repair of the spine includes a distractor and a permanently implanted bone plate system. A surgical repair methodology is also disclosed that employs an implanted bone plate system with a substantially void internal volume which is attached to adjacent vertebrae subsequent to the distraction and/or adjustment of curvature of the vertebrae and prior to the excision of disc and/or end plate tissue through the bone plate. The device further facilitates the subsequent delivery of an interbody repair device for the purpose of either fusion or dynamic stabilization, such as by disc arthroplasty. The plate may be permanently implanted, such as when a fusion between the attached vertebral bodies is desired, but it need not be permanently implanted.

8 Claims, 8 Drawing Sheets

U.S. PATENT DOCUMENTS

| | | | |
|---|---|---|---|
| 5,486,180 A | 1/1996 | Dietz et al. | |
| 5,489,307 A | 2/1996 | Kuslich et al. | |
| 5,505,732 A | 4/1996 | Michelson | |
| 5,722,977 A | 3/1998 | Wilhelmy | |
| 5,741,253 A | 4/1998 | Michelson | |
| 5,772,661 A | 6/1998 | Michelson | |
| 5,795,291 A | 8/1998 | Koros | |
| 5,797,909 A | 8/1998 | Michelson | |
| 5,800,433 A * | 9/1998 | Benzel et al. | 606/250 |
| 5,893,890 A | 4/1999 | Pisharodi | |
| 5,984,922 A | 11/1999 | McKay | |
| 6,056,749 A | 5/2000 | Kuslich | |
| 6,066,142 A | 5/2000 | Serbousek | |
| 6,080,155 A | 6/2000 | Michelson | |
| 6,096,038 A | 8/2000 | Michelson | |
| 6,102,950 A | 8/2000 | Vaccaro | |
| 6,193,721 B1 | 2/2001 | Michelson | |
| 6,207,498 B1 | 3/2001 | Chen et al. | |
| 6,224,599 B1 | 5/2001 | Baynham et al. | |
| 6,224,607 B1 | 5/2001 | Michelson | |
| 6,241,733 B1 | 6/2001 | Nicholson et al. | |
| 6,258,094 B1 | 7/2001 | Nicholson et al. | |
| 6,261,293 B1 | 7/2001 | Nicholson et al. | |
| 6,287,313 B1 | 9/2001 | Sasso | |
| 6,315,795 B1 | 11/2001 | Scarborough et al. | |
| 6,332,887 B1 | 12/2001 | Knox et al. | |
| 6,342,056 B1 | 1/2002 | Mac-Thiong et al. | |
| 6,348,058 B1 | 2/2002 | Melkent et al. | |
| 6,371,986 B1 | 4/2002 | Bagby | |
| 6,383,186 B1 | 5/2002 | Michelson | |
| 6,385,475 B1 | 5/2002 | Cinquin et al. | |
| 6,440,139 B2 | 8/2002 | Michelson | |
| 6,461,359 B1 * | 10/2002 | Tribus et al. | 606/247 |
| 6,517,544 B1 | 2/2003 | Michelson | |
| 6,558,390 B2 | 5/2003 | Cragg | |
| 6,562,046 B2 | 5/2003 | Sasso | |
| 6,562,074 B2 | 5/2003 | Gerbec et al. | |
| 6,599,292 B1 | 7/2003 | Ray | |
| 6,607,530 B1 | 8/2003 | Carl et al. | |
| 6,648,917 B2 | 11/2003 | Gerbec et al. | |
| 6,663,637 B2 | 12/2003 | Dixon et al. | |
| 6,740,087 B2 | 5/2004 | Knox | |
| 6,770,074 B2 | 8/2004 | Michelson | |
| 6,837,905 B1 * | 1/2005 | Lieberman | 623/17.16 |
| 6,859,661 B2 | 2/2005 | Tuke | |
| 6,923,811 B1 | 8/2005 | Carl et al. | |
| 7,014,633 B2 | 3/2006 | Cragg | |
| 7,033,362 B2 | 4/2006 | McGahan et al. | |
| 7,081,119 B2 | 7/2006 | Stihl | |
| 7,083,623 B2 | 8/2006 | Michelson | |
| 7,153,304 B2 | 12/2006 | Robie et al. | |
| 7,163,542 B2 | 1/2007 | Ryan | |
| 7,179,225 B2 | 2/2007 | Shluzas et al. | |
| 7,207,991 B2 | 4/2007 | Michelson | |
| 7,303,565 B2 | 12/2007 | Buttermann et al. | |
| 2003/0060825 A1 * | 3/2003 | Alfaro et al. | 606/61 |
| 2003/0060828 A1 | 3/2003 | Michelson | |
| 2003/0149341 A1 | 8/2003 | Clifton | |
| 2003/0187441 A1 | 10/2003 | Bolger et al. | |
| 2003/0236526 A1 | 12/2003 | Van Hoeck et al. | |
| 2004/0097925 A1 * | 5/2004 | Boehm et al. | 606/61 |
| 2004/0106927 A1 | 6/2004 | Ruffner et al. | |
| 2004/0106997 A1 | 6/2004 | Lieberson | |
| 2004/0204717 A1 | 10/2004 | Fanger et al. | |
| 2004/0215203 A1 | 10/2004 | Michelson | |
| 2004/0267274 A1 | 12/2004 | Patel et al. | |
| 2005/0043738 A1 | 2/2005 | Ryan | |
| 2005/0043740 A1 | 2/2005 | Haid et al. | |
| 2005/0149026 A1 * | 7/2005 | Butler et al. | 606/69 |
| 2005/0149046 A1 | 7/2005 | Friedman et al. | |
| 2005/0267481 A1 | 12/2005 | Carl et al. | |
| 2006/0036247 A1 | 2/2006 | Michelson | |
| 2006/0074424 A1 | 4/2006 | Alleyne et al. | |
| 2006/0084844 A1 | 4/2006 | Nehls | |
| 2006/0094951 A1 | 5/2006 | Dean et al. | |
| 2006/0122701 A1 * | 6/2006 | Kiester | 623/17.11 |
| 2006/0136058 A1 | 6/2006 | Pietrzak | |
| 2006/0241646 A1 | 10/2006 | Stihl | |
| 2006/0247654 A1 | 11/2006 | Berry | |
| 2006/0271198 A1 | 11/2006 | McAfee | |
| 2006/0276794 A1 | 12/2006 | Stern | |
| 2007/0173842 A1 | 7/2007 | Abdou | |
| 2007/0233107 A1 * | 10/2007 | Zielinski | 606/69 |
| 2008/0045966 A1 | 2/2008 | Buttermann et al. | |
| 2009/0143716 A1 | 6/2009 | Lowry et al. | |
| 2010/0057134 A1 | 3/2010 | Lowry et al. | |

FOREIGN PATENT DOCUMENTS

| | | |
|---|---|---|
| DE | 10307758 A1 | 9/2004 |
| FR | 2727005 A1 | 5/1996 |
| SU | 1424826 A1 | 9/1988 |
| WO | WO97/06753 A2 | 2/1997 |
| WO | WO98/14142 A1 | 4/1998 |
| WO | WO02/09626 A1 | 2/2002 |
| WO | WO02/069811 | 9/2002 |
| WO | WO03/075774 A1 | 9/2003 |

OTHER PUBLICATIONS

Lowry et al.; U.S. Appl. No. 12/210,109 entitled "Device and method for tissue retraction in spinal surgery," filed Sep. 12, 2008.

Lowry et al.; U.S. Appl. No. 12/210,089 entitled "Transcorporeal spinal decompression and repair system and related method," filed Sep. 12, 2008.

Lowry et al.; U.S. Appl. No. 12/239,431 entitled "Vertebrally-mounted tissue retractor and method for use in spinal surgery," filed Sep. 26, 2008.

Choi et al.; Modified transcorporeal anterior cervical microforaminotomy for cervical radiculopathy: a technical note and early results; Eur. Spine. J.; vol. 16; pp. 1387-1393; 2007.

George et al.; Oblique transcorporeal approach to anteriorly located lesions in the cervical spinal canal; Acta. Neurochir. (Wien); vol. 121; pp. 187-190; 1993.

George et al.; Oblique transcorporeal drilling to treat anterior compression of the spinal cord at the cervical level; Minim. Invas. Neurosurg.; vol. 37; pp. 48-52; 1994.

Hong et al.; Comparison between transuncal approach and upper vertebral transcorporeal approach for unilateral cervical radiculopathy—a preliminary report; Minim. Invas. Neurosurg.; vol. 49; pp. 296-301; 2006.

Jho et al.; Ventral uncoforaminotomy; J. Neurosurg. Spine; vol. 7; pp. 533-536; 2007.

Jho et al.; Anterior microforaminotomy for treatment of cervical radiculopathy: part 1—disc-preserving functional cervical disc surgery; Neurosurgery; vol. 51; supp. 2; pp. S-46-S-53; Nov. 2002.

Kim et al.; Anterior decompression via a wide transvertebral approach and a ceramic insert in a patient with cervical degenerative disease; Surgical neurology; vol. 67; pp. 127-134; 2007.

Wolf et al.; MBARS: mini bone-attached robotic system for joint arthroplasty; Int. J. Medical Robotics and Computer Assisted Surgery; vol. 1; No. 2; pp. 101-121; 2005.

Lowry et al.; U.S. Appl. No. 12/616,762 entitled "Implantable vertebral frame systems and related methods for spinal repair," filed Nov. 11, 2009.

Lowry et al.; U.S. Appl. No. 12/616,772 entitled "Transcorporeal spinal decompression and repair systems and related methods," filed Nov. 11, 2009.

O'Farrell et al.; U.S. Appl. No. 12/783,499 entitled "Implantable vertebral frame systems and related methods for spinal repair," filed May 19, 2010.

* cited by examiner

| Existing Method |
|---|
| Current spine exposure |
| Place distractor pins |
| Place distractor spreader |
| Perform tissue removal |
| Place interbody implant |
| Remove distractor spreader |
| Place plate |
| Attach plate to spine |

FIG. 1A

| New Method |
|---|
| Current spine exposure |
| Insert vertebral distractor |
| Place plate |
| Attach plate to spine |
| Remove vertebral distractor |
| Perform tissue removal |
| Place interbody implant |

FIG. 1B

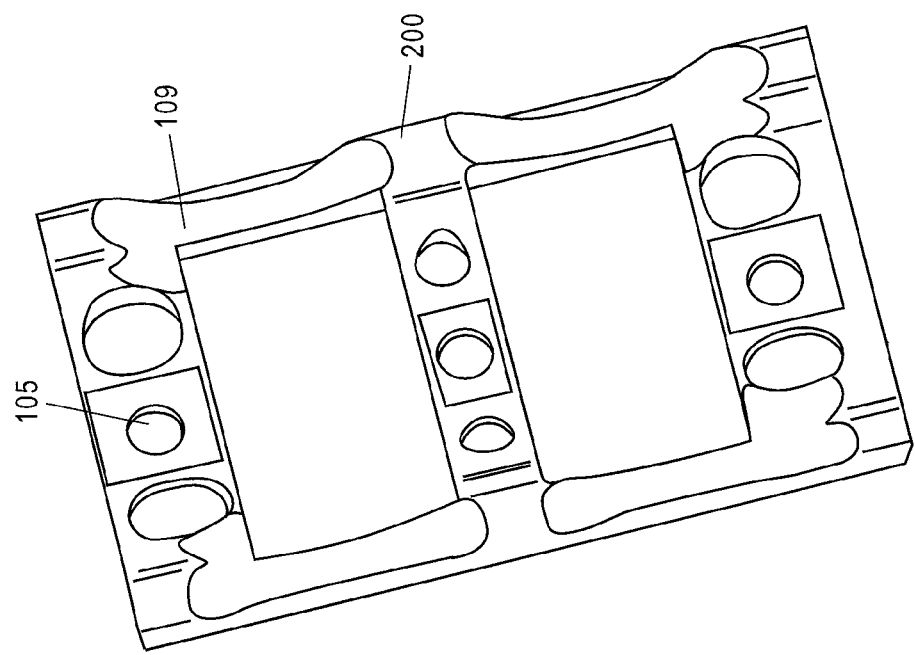
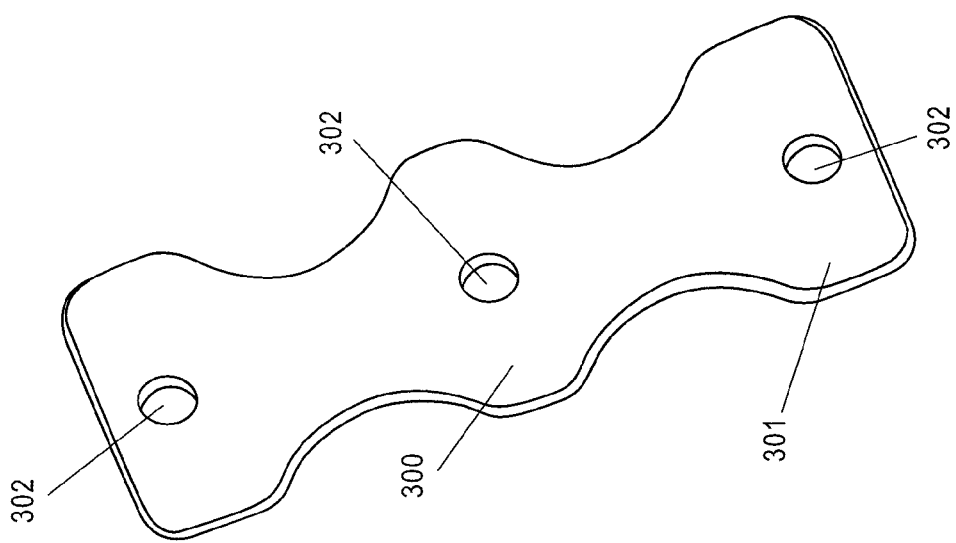
FIG. 5

IMPLANTABLE BONE PLATE SYSTEM AND RELATED METHOD FOR SPINAL REPAIR

CROSS-REFERENCE TO RELATED APPLICATIONS

This application claims priority to U.S. Provisional Patent Application Ser. No. 60/954,511 (titled "Implantable Bone Plate System and Related Method for Spinal Repair") filed Aug. 7, 2007. The provisional patent application is incorporated herein by reference in its entirety.

The present invention relates to a system for performing surgical repair of the spine, such as for but not limited to the delivery of an interbody repair device for the purpose of either fusion or dynamic stabilization.

BACKGROUND OF THE INVENTION

It is current practice in spinal surgery to use bone fixation devices to improve the mechanical stability of the spinal column and to promote the proper healing of injured, damaged or diseased spinal structures. Typically, corrective surgery entails the removal of damaged or diseased tissue, a decompression of one or more neural elements, followed by the insertion of an intervertebral implant for the purposes of a fusion or disc arthroplasty. In cases where spinal fusion is the desired surgical outcome, the final step is often to apply a bone plate in order to immobilize adjacent vertebral bones to expedite osteogenesis across said vertebral segments.

Most current surgical techniques require that damaged vertebral tissue be placed under rigid axial distraction throughout much of the procedure. This allows for greater ease in the removal of tissue, provides a larger working space for instrument maneuverability, enhances the surgeon's visibility and assists with the fit of the interbody implant once the distractor apparatus is removed. Conventional distraction of the spine typically employs the use of temporary "distractor pins" placed directly into the bone tissue adjacent to the disc space to be repaired, which are subsequently induced to move axially by the attachment and adjustment of a secondary tool. An alternative method employs the use of a ratcheting spreader device which is inserted directly into the vertebral interspace and is adjusted thereafter to achieve desired distraction. These distraction methods offer an imprecise means to restore preferred vertebral alignment, add several steps, require more time to install and remove, increase the risk for entwining of surrounding vascular structures or peripheral nerves and can present significant physical impediments and technical challenges to the surgeon. Additionally, because the distractor device remains temporarily inserted during the decompression and fusion portions of the procedure, the surgeon must essentially work around the obtrusive projecting devices while completing the majority of the surgery.

It is also known that current distraction methods, while generally not designed or intended for this purpose, are often employed to adjust or maintain the angular alignment of adjacent vertebra in an attempt to restore normal lordotic curvature. The outcomes are varied, the degree of distraction and the angular correction produced by current distraction methods are often imprecise, require substantial subjective assessment by the surgeon and can vary significantly from patient to patient. Further, excessive distraction can result in a negative surgical outcome which can result in nerve damage or on-going post surgical pain for the patient.

There is a high degree of dimensional variability in the resulting intervertebral volume after distraction has been achieved using these devices. As a result, the surgeon must often make "trial and error" assessments as to the size and shape of the interbody implant to be inserted and may be required to customize the implant intraoperatively prior to final insertion.

In the conventional method, once the implant has been inserted, the distractor device is removed and the vertebrae can be secured by the attachment of a bone plate. Such bone plates, including a plurality of bone screws, are applied near the completion of the procedure to provide vertebral fixation and prohibit undesirable migration of the intervertebral implant.

Several design constructs have already been proposed in which a device is applied to adjacent vertebrae at the start of a procedure, prior to tissue removal, for the purposes of achieving and maintaining preferred vertebral alignment while serving also to constrain tissue removal throughout the procedure. The disclosed or published art in this method can generally be categorized into two broad categories: removable devices and permanently implantable devices.

The removable devices differ from the present proposed invention in that the devices used to maintain preferred vertebral alignment are temporary inserts and are subsequently removed after tissue removal so that a repair device may be delivered thereafter. The prior art which discloses permanently implantable devices differs in that the devices function solely to maintain preferred vertebral alignment and are not part of a comprehensive system and related method to precisely control and permanently maintain the preferred spatial relationship of adjacent vertebral members for controlled tissue removal and delivery of a repair device.

Removable Devices

U.S. Pat. No. 7,153,304 entitled Instrument System for Preparing a Disc Space Between Adjacent Vertebral Bodies to Receive a Repair Device, issued Dec. 26, 2006 to Robie et al., discloses a removable instrument system for preparing a disc space between adjacent vertebral bodies using a series of distractors that restore natural lordosis before a temporary template is attached for vertebral immobilization and to function as a guide for an insertable reamer meant for tissue removal.

U.S. Pat. No. 7,083,623 to Michelson, entitled Milling Instrumentation and Method for Preparing a Space Between Adjacent Vertebral Bodies, issued Aug. 1, 2006, discloses a removable milling device and method for preparing a space between adjacent vertebral bodies which essentially maintains preferred vertebral alignment while functioning as a saw guide to control bone and soft tissue removal.

U.S. Pat. App. 2005/0043740 to Haid, entitled Technique and Instrumentation for Preparation of Vertebral Members, published Feb. 24, 2005, discloses a removable instrumentation set and technique for preparation of vertebral members utilizing a docking ring which is temporarily applied to the anterior spine to maintain preferred vertebral alignment and to function as a docking plate for an articulating bone removal device.

U.S. Pat. No. 7,033,362 to McGahan, entitled Instruments and Techniques for Disc Space Preparation, issued Apr. 25, 2006, discloses a removable instrumentation set and method for disc space preparation whereby an intervertebral device is temporarily inserted for the purpose of constraining tissue removal and guiding the position of an intervertebral repair device.

U.S. Pat. App. 2003/0236526 to Van Hoeck, entitled Adjustable Surgical Guide and Method of Treating Vertebral Members, published Dec. 25, 2003, discloses a removable surgical guide and method with adjustable functionality for the preparation of adjacent vertebra.

U.S. Pat. App. No. 2006/0247654 to Berry, entitled Instruments and Techniques for Spinal Disc Space Preparation, published Nov. 2, 2006, discloses a removable milling instrument assembly for vertebral endplate preparation which constrains a cutting path obliquely oriented to the axis of the vertebra.

Permanently Implanted Devices

U.S. Pat. App. 2004/0097925 to Boehm, entitled Cervical Spine Stabilizing System and Method, published May 20, 2004, discloses a permanently implantable spine stabilizing system and method whereby a plate configured to be positively centered along the midline is placed to retain adjacent vertebra in a desired spatial relationship during discectomy and fusion procedures. The disclosed invention uses a series of temporary implants and removable drill templates in an attempt to assure the alignment of the implanted device along the midline of the spinal column. This alignment is typically not considered to be significant in determined the clinical outcome of the procedure and is further considered impractical for the purposes of performing repair procedures on multiple adjacent disk spaces due to the normal scoliotic curvature of the spine.

U.S. Pat. App. 2005/0149026 to Butler et al., entitled Static and Dynamic Cervical Plate Constructs, published Jul. 7, 2005, describes an implanted cervical bone plate having a graft window located between the bone screw holes for the purposes of providing visualization and access to an intervertebral implant. The device described is applied after the intervertebral space has been repaired and after the implant has been positioned. The specification states specifically that an appropriately "sized dynamic plate is placed over the inserted bone implant"; thereafter the bone plate is located with respect to the implant by viewing the implant through the graft window and secured in place using bone screws.

Accordingly, it is apparent that there remains a need for and advantage to a permanently implantable spinal repair system and related method whereby the final preferred vertebral alignment and fixation occurs prior to the surgical removal of damaged tissue, without the use of temporary implants or fasteners and where the surgical procedures can be performed there-through in the minimum amount of time with the minimum number of entries into the surgical field. It is further apparent that there is a need for a system wherein subsequent recovery procedures can be performed with minimal effort should implantation fail or should subsequent surgery be required.

SUMMARY OF THE PRESENT INVENTION

The invention relates generally to systems and methods for establishing and securing adjacent vertebrae in a defined spacial relationship prior to the excision and repair of damaged tissue. In one embodiment, the system includes at least one distraction device, at least one implantable vertebral frame, at least one interbody repair implant, and at least one retention member. In this embodiment, the distraction device is configured for temporary placement between adjacent vertebrae for achieving a desired spatial relationship between the vertebrae. In this embodiment, the implantable vertebral frame is configured to span between the adjacent vertebrae, the frame being configured to attach to each of the adjacent vertebra while the distraction device is in place to postoperatively maintain the desired spatial relationship between the vertebrae after the distraction device is removed, the frame also having at least one internal operating aperture there-through for providing access to at least one intervertebral disk space. In this embodiment, the interbody repair implant is sized in relationship to the aperture of the frame to fit there-through and into the intervertebral space. And finally, in this embodiment, the retention member is attachable to the frame to cover at least a portion of the aperture.

In various embodiments of the above summarized system, the frame may assume various forms and include various features that will now be summarized. In some embodiments of the system, the frame may be configured to span between and remain postoperatively attached to at least three adjacent vertebrae. In some embodiments of the system, the frame may include external walls having integrally manufactured retractor blade engaging features. In some embodiments of the system, the frame may have a plurality of through holes to facilitate attachment of the frame to adjacent vertebrae by means of bone screws. In some of these particular embodiments, the holes may be a combination of elongated slots and circular holes to accommodate the insertion of bone screws there-through into vertebral bone tissue. In some embodiments of the system, the frame may have a plurality of protrusions to facilitate attachment of the frame to the adjacent vertebrae by means of impingement into the bone tissue of the adjacent vertebrae.

Further, in some embodiments of the system, the frame may have one or more receiving elements to accept a locking member for securing the retention member. In various of these particular embodiments, the locking member may be any of a threaded screw device, a snap lock device, or a cam lock device, and further in some of these particular embodiments, the one or more receiving elements for the retention member may accommodate the temporary location of at least one tissue retractor pin.

Still further, in some embodiments of the system, the frame may be configured to receive bone screws there-through to attach the frame to the vertebrae, the retention member being adapted to cover the bone screws when the member is attached to the frame to prevent back-out of the screws.

In some embodiments of the system, the retention member may be configured to retain the interbody implant in its surgically established position.

According to an aspect of the invention, a vertebral implant may be provided. Embodiments of the implant are configured to rigidly interconnect at least two vertebrae, the implant being manufactured from a generally rigid material having thereon contact surfaces for engaging on vertebral bone material, the contact surfaces including a biocompatible, compressible, polymeric material. In some of these embodiments, the generally rigid material may also include a biocompatible metallic material.

In another aspect of the invention, various embodiments of methods are provided for applying the system and/or the vertebral implant, as summarized above. In one method of applying the system, the adjacent vertebrae are distracted and spacially oriented with the distraction device, the vertebral frame is secured to the adjacent vertebrae, the damaged tissue is excised through the operating aperture in the vertebral frame, the vertebral interspace is prepared to receive the repair implant, said implant being placed through the operating aperture into said prepared interspace, and the retention member is then installed onto the vertebral frame.

Another embodiment of a method for applying the system is also provided. In this embodiment, the vertebral frame is attached to one or more vertebrae, the vertebrae are then distracted and spacially oriented by operating through the operating aperture in the vertebral frame, the vertebral frame is secured to each adjacent vertebrae, the damaged tissue is excised through the operating aperture in the vertebral frame, the vertebral interspace is prepared through the operating aperture to receive the repair implant, the interbody implant is inserted through the operating aperture into the prepared interspace and the retention member is installed onto the vertebral frame.

In another aspect of the invention, a method for treating a portion of a spinal column is provided. The method includes distracting and spacially orienting adjacent vertebral bodies of the spinal column, securing a vertebral frame to the adjacent vertebral bodies, the vertebral frame having at least one operating aperture there-through, preparing a vertebral interspace to receive an interbody implant, inserting the interbody implant through the operating aperture and into the prepared interspace, and maintaining the vertebral frame in place on the vertebral bodies postoperatively.

In some embodiments of this method for treating a portion of a spinal column, the distracting step is performed using a distraction device placed between the vertebral bodies, and the distraction device is removed from between the vertebral bodies through the operating aperture in the vertebral frame after the vertebral frame is secured to the vertebral bodies. In some of these methods for treating a portion of the spinal column, the method may further include the step of excising damaged tissue through the operating aperture in the vertebral frame. In another embodiment, the method may further include the step of installing a retention member onto the vertebral frame after inserting the interbody implant. In still other embodiments, the step of preparing a vertebral interspace to receive an interbody implant may be performed through the operating aperture of the vertebral frame.

In some embodiments of the method for treating a portion of the spinal column, the vertebral frame may have particular features or aspects. Thus, in some embodiments, the vertebral frame may be attached to at least one of the vertebral bodies before the distraction step, the distraction step being performed through the operating aperture in the vertebral frame. In other embodiments, the vertebral frame may be secured to more than two adjacent vertebral bodies. In still other embodiments, the vertebral frame may be maintained in place permanently, generally from the time it is first secured to the vertebral bodies.

According to some aspects of the present invention, a means and method to precisely control and permanently maintain the preferred spatial relationship of adjacent vertebral members prior to the surgical removal of damaged tissue may be provided.

According to some aspects of the invention, a means may be provided whereby preferred spatial relationship of adjacent vertebra can be achieved and permanently maintained using conventional vertebral distraction methods or in conjunction with a novel intervertebral distractor apparatus disclosed separately in the patent application Ser. No. 60/954,507 titled "Device and Method for Variably Adjusting Intervertebral Distraction and Lordosis" filed on Aug. 7, 2007.

According to some aspects of the invention, the surgical removal of damaged tissue may be constrained in order to minimize the risk of damage to the adjacent tissue.

According to some aspects of the invention, the preferred spatial relationship of adjacent vertebral members may be precisely controlled and permanently maintained with a device having a low profile, allowing the surgeon to work in an unrestricted manner, within, around, above and below the device.

According to some aspects of the invention, the preferred spatial relationship of adjacent vertebral members may be precisely controlled and permanently maintained for the insertion of a spinal repair device.

According to some aspects of the invention, the insertion of a spinal repair device may be spatially controlled.

According to some aspects of the invention, a locking member may be accommodated to prevent undesirable migration of the spinal repair device and bone screws.

According to some aspects of the invention, the method and device may be utilized across one or multiple vertebral segments.

According to some aspects of the invention, a permanent rigid internal fixation may be provided across one or multiple vertebral segments.

In one particular embodiment, a permanent semi-rigid fixation is provided across one or multiple vertebral segments.

In one particular embodiment, a retractor apparatus is accommodated by providing integrally manufactured receiving and engaging means for the tissue control blades of said retractor.

In one particular embodiment, removable templates which locate and constrain the surgical removal of tissue to the desired vertebral area are accommodated.

In one particular embodiment the vertebral fixation element in the system is manufactured using two biocompatible materials, the structural component being manufactured from a high modulus rigid material such as Titanium, Stainless steel or other metal and having therein contact elements for engaging on the vertebral tissue, said contact pads being manufactured from a bio-compatible compliant material such as polyethylene or a silicone. These contact pads are intended to be plastically deformed under compressive loads and to be compressed and deformed by the insertion of the bone screws in order to act as damping elements to absorb vibration during bone tissue removal and consequently to minimize the risk of associated screw dislocation. These pads further increase the initial friction between the vertebral fixing element and the vertebrae thereby reducing premature dynamic compression of the distracted vertebrae. Finally, the compliant elements act as shock absorbers during patient healing and promote osteogenesis within the implanted repair device.

In one particular embodiment, the inventive device may be coupled with a stereotactic navigational system for preferred device positioning and to constrain the surgical removal of tissue.

DESCRIPTION OF INVENTION

The invention described herein includes a system and surgical method for use in surgical spinal repair or reconstruction procedures whereby preferred and final vertebral axial and angular positioning and fixation occurs prior to the cutting and removal of the tissue.

In one embodiment, the system can generally be described as a combination of:

1) An intervertebral distraction device placed temporarily between adjacent vertebrae for purposes of achieving a desired spatial relationship between adjacent vertebrae.
2) A vertebral plate.
3) A locking and retention member engaging with said vertebral plate.
4) An implantable interbody repair device.
5) Bone screws.

6) The vertebral plate having through holes for the purposes of accommodating attachment to the vertebrae using the bone screws.
7) Said vertebral plate having a generally open interior volume through which the removal of damaged tissue is performed.
8) Said vertebral plate having a generally open interior volume which constrains the insertion and prevents migration of an intervertebral repair device.
9) Said vertebral plate having accommodation means for attaching the locking and retention member for retention of the implanted repair device and the bone screws.
10) One embodiment of the surgical method may be generally described as the sequence of spacially orienting adjacent vertebrae, locking said vertebrae in their prescribed relative positions using the vertebral plate and bone screws, preparing and repairing the intervertebral space through the operating window in the installed vertebral plate and securing the implant in place by securing a locking member to the vertebral plate.
11) An alternate surgical method may be generally described as the sequence of attaching the vertebral plate to one of the adjacent vertebrae, spacially orienting the adjacent vertebrae through the operating window in the vertebral plate, locking said vertebrae in their prescribed relative positions using the vertebral plate and bone screws, preparing and repairing the intervertebral space through the operating window in the installed vertebral plate and securing the implant in place by securing a locking member to the vertebral plate.
12) In an alternate surgical method, the vertebrae are partially distracted and held in this position by the insertion of bone screws through slots in the vertebral plate. In this instance the final distraction is achieved by the forcible insertion of an interbody repair device which has a cranio-caudal dimension that is larger than the dimension of the receiving intervertebral space. The differences in the two dimensions results in a further, final distraction of the adjacent vertebrae. This final movement of the vertebrae is accommodated by the movement of the screws within the slots in the vertebral plate.

In an anticipated procedure a conventional intervertebral distractor apparatus is manually inserted into or between the vertebrae resulting in axial distraction of the vertebrae. In the case of a standard wedge style distractor the degree of distraction results from a combination of the included angle and the depth to which it is inserted between the vertebrae. In the case of a distractor pin system the distraction results from the manipulation of a secondarily applied axial adjustment device.

In a further embodiment the included angle of the distractor device is variably adjustable by the surgeon after insertion between the vertebrae, this adjustment being achieved mechanically by means of a screw adjustment or the use of another adjusting tool. Such a distractor device is disclosed in the application Ser. No. 60/954,507 titled "Device and Method for Variably Adjusting Intervertebral Distraction and Lordosis" filed on Aug. 7, 2007.

In a further embodiment the distractor apparatus can be mated with a stereotactic navigational device to establish, monitor and control the positioning of the device relative to the adjacent vertebra.

After distraction and lordotic adjustment has been achieved the spinal bridge is located on the vertebrae relative to the distractor device and attached to the adjacent vertebra by at least two bone screws, securing the vertebrae in their prescribed positions.

If intervertebral distractor devices have been employed they are removed, exposing a predefined accessible and constrained operating field allowing the controlled cutting and removal of tissue to occur.

In a further embodiment the vertebral plate can accommodate insertable control templates which can be placed within it by the surgeon to further assist precise tissue removal.

In a further embodiment the vertebral plate can serve as a mounting base for the attachment of soft tissue retractors, further aiding the surgeon by assuring an un-impeded surgical field.

In a further embodiment the vertebral plate can be removed after the placement of a disc arthroplasty device.

The intervertebral repair device may be generally wedge shaped, it may have an initial radius or taper for engagement with the adjacent vertebrae or it may be conically or cylindrically shaped.

Further, this device may have surface contours thereon which are intended to increase the surface area of contact between said surfaces and the exposed cancellous bone tissue and to increase the intimate compressive engagement with said cancellous tissue so as to induce and encourage osteogenesis therein.

BRIEF DESCRIPTION OF THE DRAWINGS

FIG. 1a shows the typical sequence of steps in a current surgical procedure.

FIG. 1b shows the sequence of one embodiment of the inventive method herein.

FIG. 5 illustrates a retention member relative to the vertebral frame.

DETAILED DESCRIPTION OF THE INVENTION

FIG. 1a describes the typical operational sequence currently employed, wherein vertebrae are distracted, tissue is excised, an implant in placed between adjacent vertebrae and a bone plate is attached. FIG. 1b describes the preferred operational sequence associated with this invention, wherein vertebrae are distracted and placed in their preferred relative angular positions and a vertebral frame is attached to adjacent vertebrae using bone screws to maintain the prescribed spatial relationship during the subsequent steps. In an alternative sequence, the vertebral frame may be attached to adjacent vertebrae prior to distraction and preferred positioning. Thereafter tissue is excised though the aperture in the frame, the implant is inserted through said aperture. A retaining member may be attached to said vertebral frame to maintain the position of the implanted insert and to prevent back-out of the bone screws.

Figure 2A:
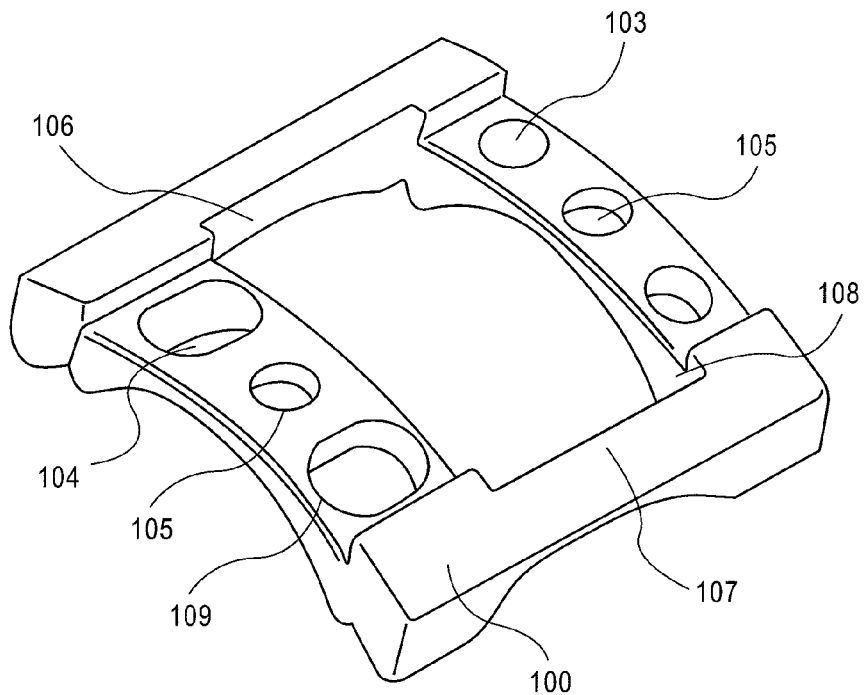
FIG. 2a is an anterolateral isometric view of a single level implantable bone plate.
Figure 2B:
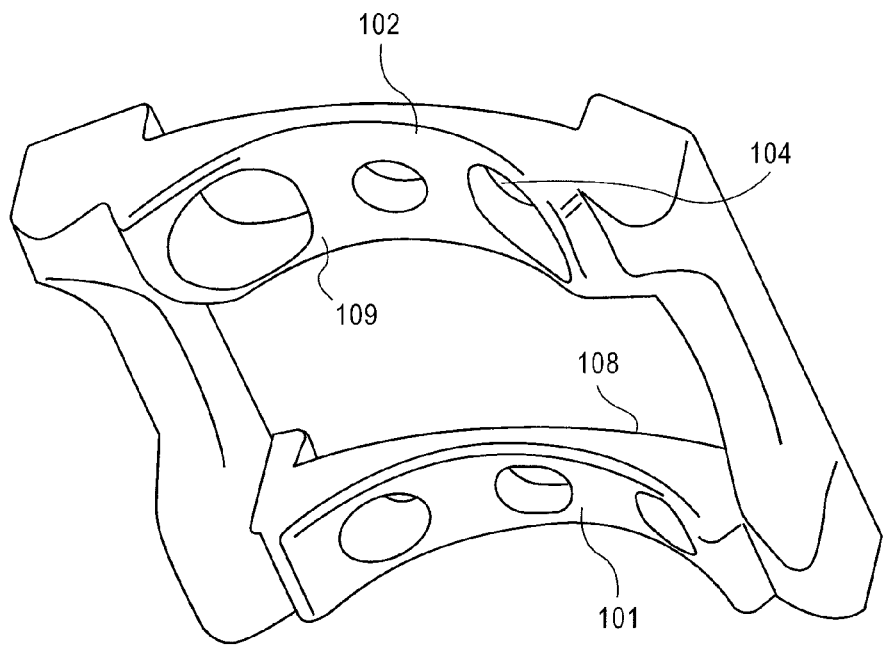
FIG. 2b is a posterolateral isometric view of a single level implantable bone plate.

FIGS. 2a and 2b depict a single level vertebral frame, intended to secure two adjacent vertebrae. The device has surfaces 101 and 102 which are generally contoured to engage positively with the anterior surfaces of the adjacent vertebrae. The device has through holes 103 and 104 intended to accommodate the insertion of bones screws into the vertebral tissue. Holes 104 may be elongated to accommodate post surgery dynamic settling of the vertebrae. The device further has one or more holes 105 intended for receiving screws (or other fixation devices) securing the retaining member thereto or there-through. The receiving holes 105 also provide a mounting means for the insertion of temporary soft tissue retractor pins. The device has an operating window defined by the side walls 106, 107, 108 and 109. This window is intended to allow unimpaired access to the intervertebral space in order to excise tissue and subsequently to allow the insertion of the interbody repair device there-through.

Figure 3A:
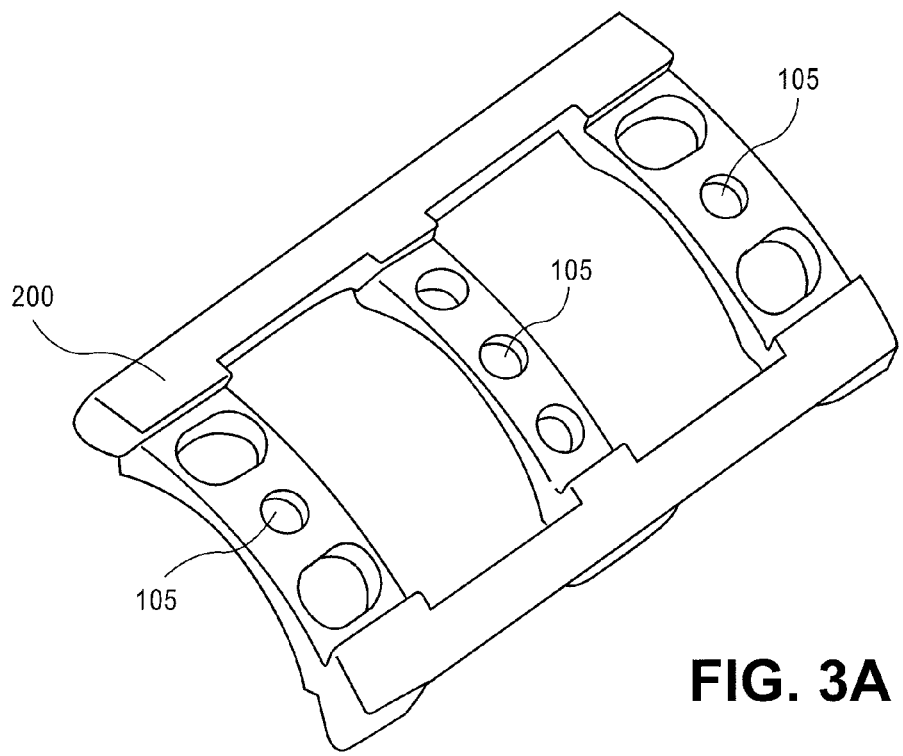
FIG. 3a is an anterior isometric view of a multi-level implantable bone plate.

FIG. 3a depicts a multi-level vertebral frame 200, intended to facilitate the orientation, fixation and repair of three or more vertebrae.

Figure 3B:
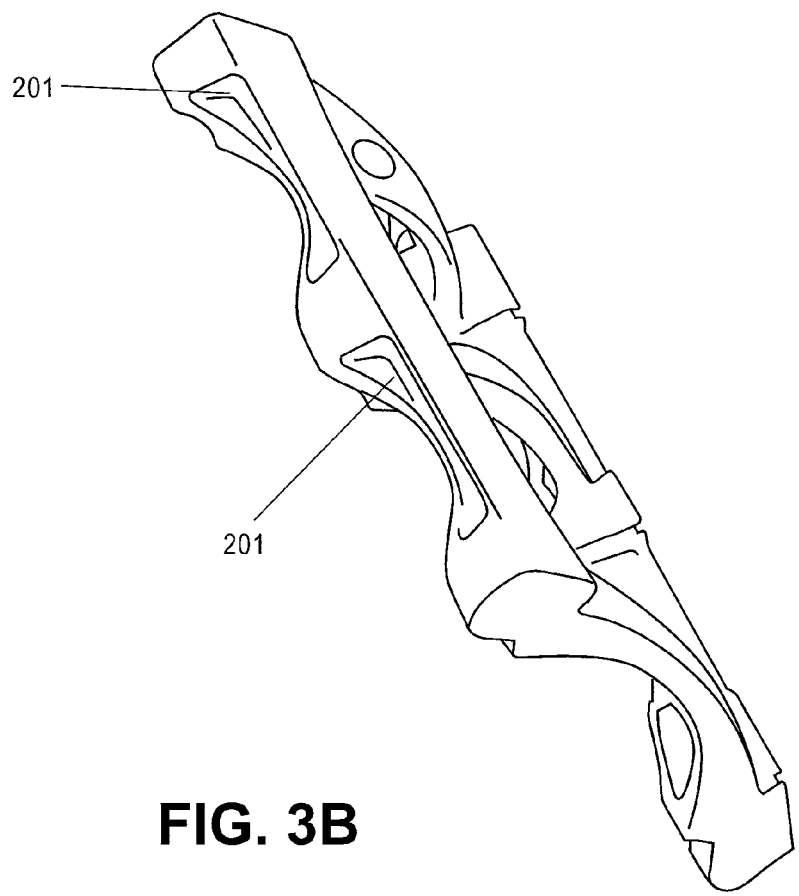
FIG. 3b is a lateral isometric view of a multi-level implantable bone plate.

FIG. 3b depicts a side view of a multilevel device and illustrates the presence of a receiving means 201 on the vertebral frame, thereby permitting the plate to accommodate the location and retention of soft tissue retractor blades.

Figure 4:
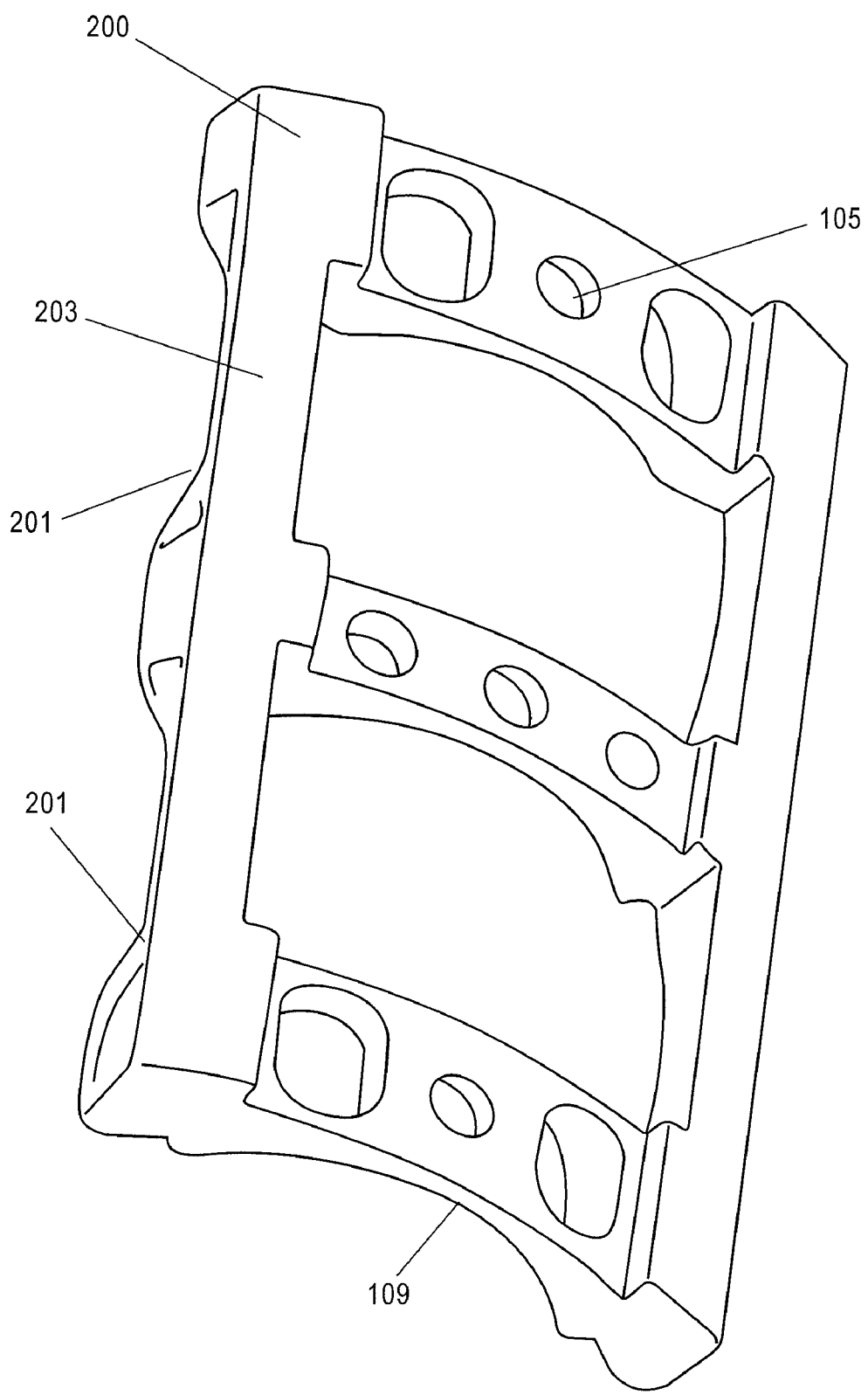
FIG. 4 is an oblique perspective view of a multi-level bone plate.

Referencing FIGS. 4 and 5; the retention member 300 has a posterior surface 301 contoured to match the anterior surface of the vertebral frame 200 and through holes 302 which align with the receiving holes 105 in the vertebral frame, these holes being intended to secure the retention member 300 to the vertebral frame 200 in order to retain the interbody implant in position and to prevent the back-out of the bone screws used to secure frame 200 to the vertebral bone tissue.

Figure 6:
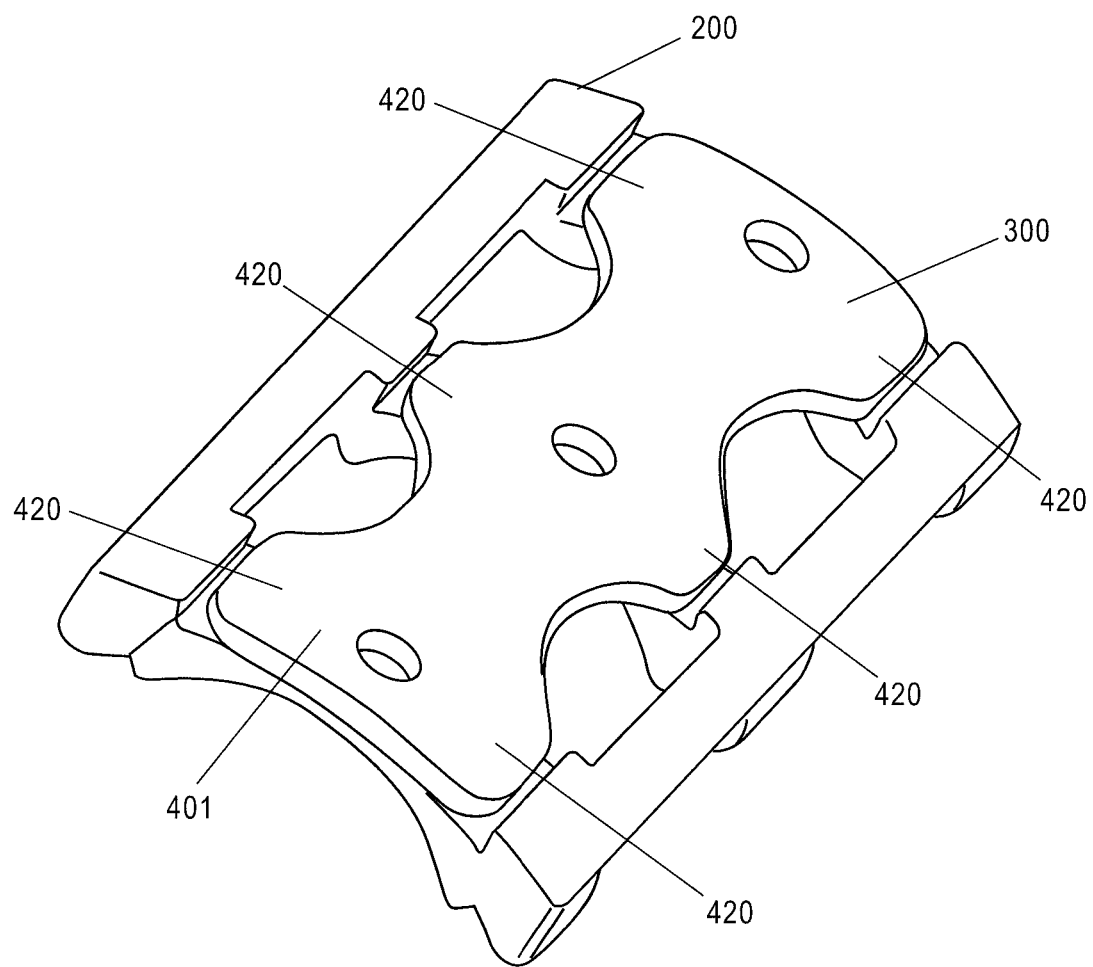
FIG. 6 depicts a retention member in an installed position on the vertebral frame.

FIG. 6 shows retention member 300 installed to the vertebral frame 200, the anterior surface of the retention member having a contour 401 which generally matches that of the vertebral frame 200 to create a smooth, continuous surface after installation.

FIG. 6 further shows the retention member having extensions 420 that cover the bone screws and thereby preventing screw back-out.

Figure 7:
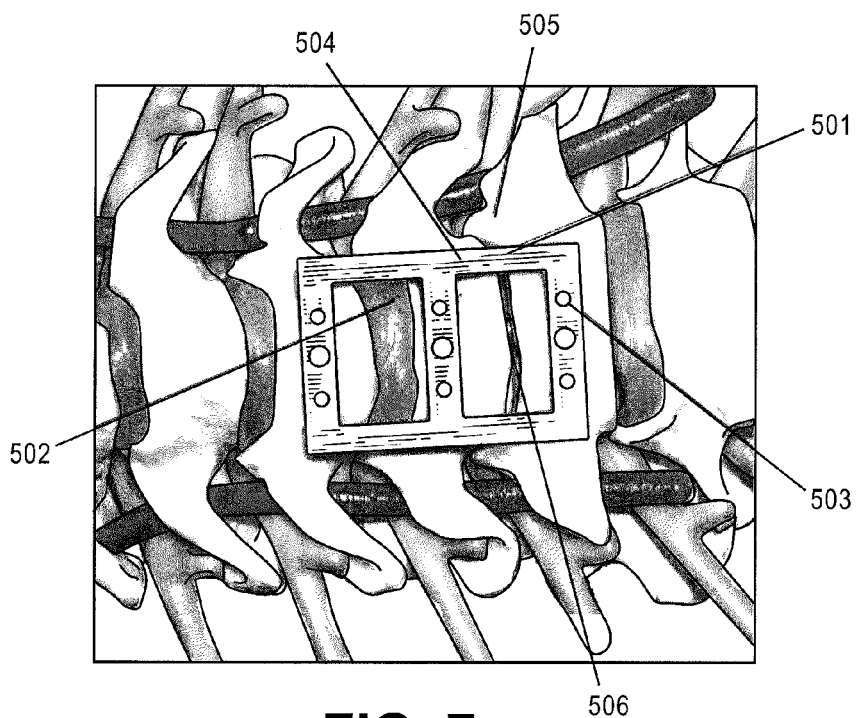
FIG. 7 is an anterior (surgical) view of a vertebral frame in its installed position on adjacent vertebrae.

FIG. 7 depicts the vertebral frame in position on adjacent vertebrae and illustrates the operating window in the region of the disk space. The operating window is defined by the cross members 503, 504, 505 and 506 respectively which produce a contained area through which all procedures may be executed. Further, these members act to restrain the surgeon during tissue excision and thereby minimize the risk of accidental damage to surrounding tissue.

FIG. 7 further illustrates how the device provides access to facilitate the removal of disk material 502 and the preparation of the intervertebral space 501 prior to the insertion of the interbody implant.

Figure 8:
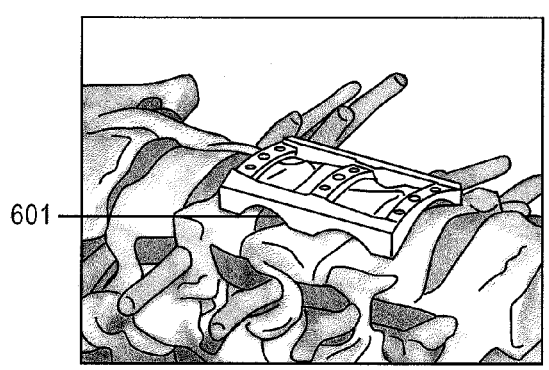
FIG. 8 is an anterolateral perspective view of the vertebral frame in its installed position on adjacent vertebrae.

FIG. 8 is a perspective side view of the vertebral frame in the installed position on adjacent vertebrae. The device has clearance spaces 601 in the region of the disk material to accommodate a better fit to the vertebral surfaces and to provide additional clearance to allow for the removal of unwanted bone material after device installation.

Figure 9:
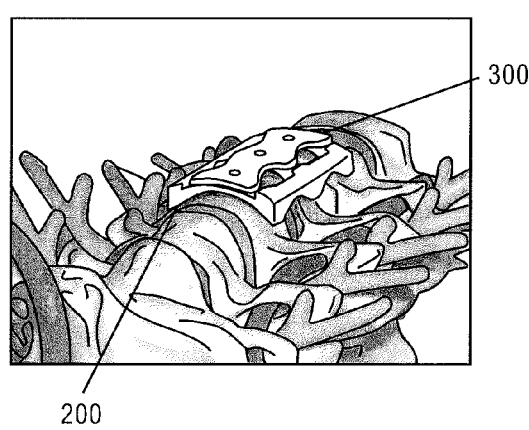
FIGS. 9 and 10 depict a retention member in-situ after installation onto the vertebral plate.
Figure 10:
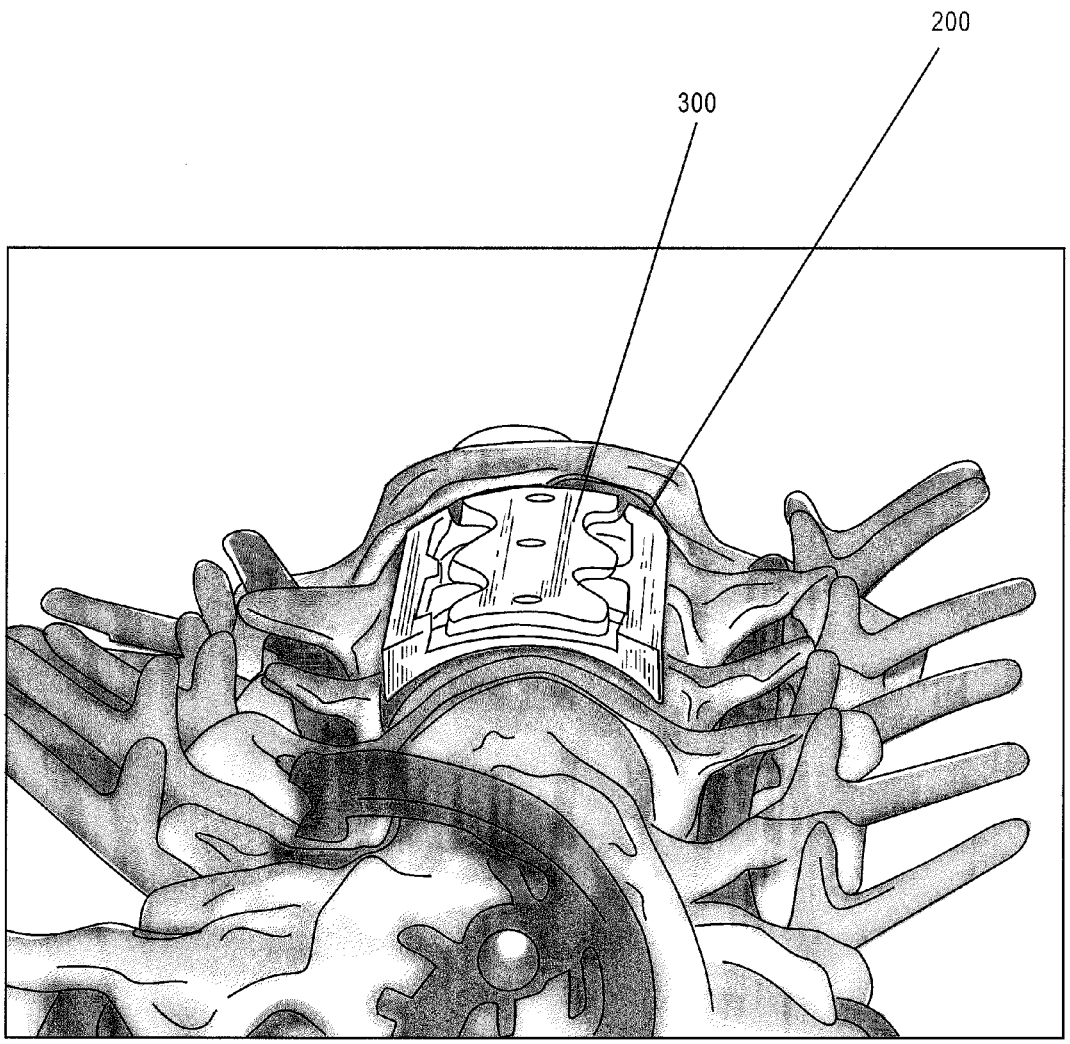

FIGS. 9 and 10 depict the retention member 300 placed in-situ on the vertebral frame 200 after the insertion of the interbody implant. The member 300 is located so as to prevent substantial movement of the interbody implant and thereby promote bone tissue growth therein.

Instead of screws, or in combination therewith, one or more snap lock devices may be used to attach retention member 300 to vertebral frame 200. Such devices may employ a compressible feature, such as a split barb, that locks into place when inserted sufficiently into hole 105 or other mating feature. By using snap lock device(s), member 300 can be simply aligned with frame 200 and pressed into place without requiring the surgeon to align screws and install them with a driver. One or more cam lock devices may also be used, alone or with screws and/or snap lock devices. In some cam lock embodiments a torsional force is applied to a component, inducing rotation and causing it to become engaged in a corresponding feature within a receiving element. This twisting action causes the component to turn and lock under another component, again with less effort than required when installing a screw.

The system offers substantial benefits over those previously disclosed and those currently employed. These benefits include, but are not limited to:

1) A novel method which allows for precise control and fixation of optimal vertebral position.
2) Constrained and controlled tissue removal
3) Elimination of patient to patient variation
4) Integration of soft tissue retraction devices
5) Reduction in surgical time and maneuvers throughout the case.

All publications and patent applications mentioned in this specification are herein incorporated by reference to the same extent as if each individual publication or patent application was specifically and individually indicated to be incorporated by reference.

What is claimed is:

1. A method of fusing two or more adjacent vertebral bodies in a portion of a spinal column, the method comprising:

axially distracting adjacent vertebral bodies of the spinal column into a final prescribed spatial relationship using a distraction device placed between the vertebral bodies and engaging upon vertebral end plate tissue;

after the vertebral bodies have been placed into their final prescribed spatial relationship in the distracting step, placing a vertebral fixation frame on the distracted adjacent vertebral bodies over the distraction device;

securing the vertebral fixation frame to the distracted adjacent vertebral bodies over the distraction device such that the vertebral bodies are maintained in their final prescribed spatial relationship after the fixation frame securing step is complete, the vertebral fixation frame configured to contact a surface of each of the vertebral bodies and comprising an implantable plate having at least one operating aperture there-through;

after the fixation frame securing step is complete, removing the distraction device from between the vertebral bodies through the operating aperture in the vertebral frame;

after the distraction device removing step, preparing a vertebral interspace to receive an interbody fusion implant by at least removing vertebral disc material through the aperture in the secured vertebral fixation frame, the adjacent vertebral bodies remaining in their final prescribed spatial relationship during the preparing step;

inserting the interbody fusion implant through the operating aperture and into the prepared interspace, the implant being configured to compressively engage opposing inferior and superior surfaces of the adjacent vertebral bodies as the implant is being inserted; and maintaining the vertebral fixation frame in its originally secured position on the vertebral bodies postoperatively.

2. The method of claim 1, further comprising the step of excising bone material through the operating aperture in the vertebral frame.

3. The method of claim 2, wherein the step of excising bone material is performed entirely through the operating aperture of the vertebral frame.

4. The method of claim 1, further comprising the step of installing an interbody implant retention member onto the vertebral frame.

5. The method of claim 1, wherein the vertebral frame is secured to more than two adjacent vertebral bodies.

6. The method of claim 1, wherein the vertebral frame is maintained in an installed position permanently, generally from the time it is first secured to the vertebral bodies.

7. The method of claim 1, wherein the distraction device engages directly upon the vertebral end plate tissue when the distraction device is placed between the vertebral bodies.

8. The method of claim 1, wherein the distraction device is placed between the vertebral bodies such that at least a portion of the distraction device is located directly between the vertebral bodies.

* * * * *